(12) United States Patent
Bremer et al.

(10) Patent No.: US 6,555,379 B1
(45) Date of Patent: Apr. 29, 2003

(54) DEVICE FOR MONITORING A PROCESSING LIQUID

(75) Inventors: Karl-Guenter Bremer, Eschweiler (DE); Thomas Hoefler, Stuttgart (DE); Peter Holzhauer, Stuttgart (DE); Thomas Netsch, Louisville, KY (US); Eckehard Walitza, Aalen (DE)

(73) Assignee: Filterwerk Mann & Hummel GmbH, Ludwigsburg (DE)

(*) Notice: Subject to any disclaimer, the term of this patent is extended or adjusted under 35 U.S.C. 154(b) by 0 days.

(21) Appl. No.: 09/581,421

(22) PCT Filed: Dec. 11, 1998

(86) PCT No.: PCT/EP98/08077

§ 371 (c)(1),
(2), (4) Date: Sep. 8, 2000

(87) PCT Pub. No.: WO99/30869

PCT Pub. Date: Jun. 24, 1999

(30) Foreign Application Priority Data

Dec. 13, 1997 (DE) .......................................... 197 55 477

(51) Int. Cl.$^7$ .............................................. G01N 35/08
(52) U.S. Cl. .......................... 436/55; 436/62; 436/138; 435/4; 435/29; 435/31; 435/34; 422/62; 422/2; 422/3; 422/79; 422/82.01
(58) Field of Search .......................... 436/55, 62, 138; 435/34, 29, 4; 422/1–3, 62, 79, 82.07

(56) References Cited

U.S. PATENT DOCUMENTS

| | | | | |
|---|---|---|---|---|
| 3,565,786 A | * | 2/1971 | Brown et al. | 196/14.5 |
| 3,750,847 A | * | 8/1973 | Sluhan | 184/109 |
| 4,053,743 A | * | 10/1977 | Niemi | 700/267 |
| 5,224,051 A | * | 6/1993 | Johnson | 700/169 |
| 5,441,873 A | * | 8/1995 | Knight et al. | 435/34 |
| 5,506,791 A | * | 4/1996 | Hungerford | 364/510 |
| 5,514,968 A | * | 5/1996 | Spanjers | 205/782.5 |
| 5,518,590 A | * | 5/1996 | Fang | 205/780.5 |
| 5,832,411 A | * | 11/1998 | Schaltzmann et al. | 702/23 |

FOREIGN PATENT DOCUMENTS

| | | | |
|---|---|---|---|
| JP | 54129180 A | * | 10/1979 |
| JP | 09085577 A | * | 3/1997 |
| WO | WO-97/43027 | * | 11/1997 |

* cited by examiner

Primary Examiner—Jill Warden
Assistant Examiner—Yelena Gakh
(74) Attorney, Agent, or Firm—Crowell & Moring LLP

(57) ABSTRACT

A device for monitoring a processing liquid comprising at least one sensor for generating at least one monitoring signal, and a device for processing the monitoring signal and for generating a control signal for directly or indirectly influencing the composition or condition of the processing liquid. A device is also provided for detecting, storing, and maintaining the reliability of performance of the sensor. In addition, actuators are provided for converting given criteria or specified values.

7 Claims, 3 Drawing Sheets

DEVICE FOR MONITORING A PROCESSING LIQUID

BACKGROUND OF THE INVENTION

The invention relates to a device for monitoring a processing liquid.

From U.S. Patent Document U.S. Pat. No. 5,224,051, a process is known for monitoring a processing liquid. This process is used particularly on a metal processing system, where a plurality of metal processing machines are provided as well as a centrally disposed reservoir which contains the quantity of hydrous cooling lubricant liquid. The metal processing machines are supplied centrally from this reservoir. The cooling lubricant liquid consists of the lubricant and hydrous constituents. These constituents are monitored, and measuring signals are generated which reach an analyzing apparatus. On the basis of the analysis, a modification takes place of the content of a constituent in the monitored liquid.

The process described in the above-mentioned patent shows an apparatus by means of which the content of dissolved oxygen is determined as a reference to microorganisms. Likewise, the conducting capacity, the pH-value and the temperature are determined. However, no information is obtained there concerning the correlation between the oxygen consumption and the microorganism load. It is a disadvantage of this system that a reliable assignment of the measured data to the constituents of the processing liquid cannot be made. For this reason, it is very difficult to meter in additional constituents or to modify the processing liquid.

It is a disadvantage of this known device that certain parameters in the liquid are very difficult to detect. Thus, for example, the detection of the microorganisms contained in the liquid can often be carried out only indirectly. In addition, there is the risk that the measuring signal is mutilated or the operability of the sensor is impaired as the result of suspended solids as well as chemically dissolved substances in the processing liquid.

Furthermore, from German Patent Document DE 43 06 184, a process is known for the continuous detection of physical or chemical parameters of liquids. The publication essentially relates to a valve arrangement which is suitable for the removal or metered addition of liquid. A processing of signal quantities and an analysis of these signals is not found in this publication.

SUMMARY OF THE INVENTION

It is an object of the invention to provide a device for monitoring a processing liquid, which is suitable for detecting several constituents in the liquid also under more difficult conditions, that is, also in the case of processing liquids with suspended solids and chemically contaminated processing liquids.

This object is achieved by the invention as described and claimed hereinafter.

The substantial advantage of the invention is the fact that first a device is provided for maintaining the operability of the sensor or sensors. Only when the sensor characteristics are constantly analyzed can informative measuring values be determined. The measuring values reach a device for processing the monitoring signals in order to indirectly or directly from these processed signals influence the composition of the processing liquid.

By means of this device, an optimal stabilization of the processing liquid is achieved and thus a long useful life of this liquid is ensured.

In order to determine the various measurable variables, certain specific sensors are conceivable. For measuring the temperature, for example, a PT 100 sensor is suitable. The concentration of the processing liquid can be determined from the combination of the refractive index and the density or of the UV cloudiness and the density. Foreign oil can also be determined by way of a combination of the refractive index and the density or the cloudiness and the density. Aerobic germs can be determined by way of a corresponding $O_2$-sensor. The pH-value is normally sensed by means of a pH electrode; the conducting capacity is determined by means of a conducting capacity sensor. The corrosiveness of the processing liquid can be determined by means of a redox electrode.

The composition of the processing liquid is influenced, for example, by means of defined control algorithms by means of an expert system or by means of neuronal networks. It is naturally also conceivable to use a fuzzy logic which carries out an optimization operation with respect to the quality of the processing liquid.

The processing liquid is advantageously monitored in a processing tank. This monitoring can be carried out, for example, by a mobile servicing apparatus suitable for field use. Naturally, variants of the apparatus are conceivable, such as a partially mobile apparatus which supplies the detected data to a remote diagnosis.

In accordance with one embodiment of the invention, the processing liquid is monitored in one or several processing tanks. It is also possible to arrange tanks side-by-side with a processing tank in order to ensure particularly favorable environmental conditions there. Advantageously, sensors can be used which sense the loading of the processing liquid with suspended solid particles. In addition, it is expedient to detect the microorganisms, the pH-value or the corrosiveness, or additional relevant quantities, such as germs, yeast fungi, bacteria, abrasiveness, nitrate, nitrite, water hardness, interfering ions, dispersed air, foam, foreign oil, foreign substances, temperature, conducting capacity in the processing liquid.

It is an object of a further refinement of the invention to carry out a remote data transmission. By way of this remote data transmission, for example, by way of a corresponding modem, monitoring signals are supplied to one or several devices for the purpose of an analysis. An integrated data analysis is also conceivable.

In addition to the device for monitoring the process liquid, an advantageous embodiment of the invention provides a filtering system for a mechanical purification. This filtering system consists, for example, of a band pass filtering system or a vacuum filter as well as additional suitable systems/apparatuses and peripheral devices.

If the processing liquid must be separated into specific constituents, for example, for the purpose of disposal, a system may be provided in another embodiment of the invention which, for example, carries out an emulsion separation. Such systems normally operate on a membrane basis (ultrafiltrate) or on a thermal or chemical basis.

An important building block in the device for monitoring processing liquid is the sensing of an aerobic infestation. The latter correlates with the oxygen consumption in the processing liquid. The oxygen consumption caused by aerobic germs is directly related to the germination index (microbiologically expressed in column-forming units per milliliter). However, the oxygen consumption in the case of a given constant aerobic germ involvement is a function of the temperature. It is therefore useful to determine the correlation between the oxygen consumption, the germination index and the temperature. Naturally, the oxygen consumption can be determined only in a closed system. It is therefore necessary to feed the processing liquid separately to a testing tank and to carry out the measuring of the oxygen consumption there.

These and other features of preferred embodiments of the invention are found, in addition to the claims, in the description and the drawings, in which case the individual features can be implemented separately or combined in the form of subcombinations in the embodiment of the invention and in other fields and can represent advantageous embodiments which are patentable by themselves, for which protection is claimed here.

The invention will be explained in more detail hereinafter with reference to a embodiment.

DETAILED DESCRIPTION OF PREFERRED EMBODIMENTS

Figure 1:
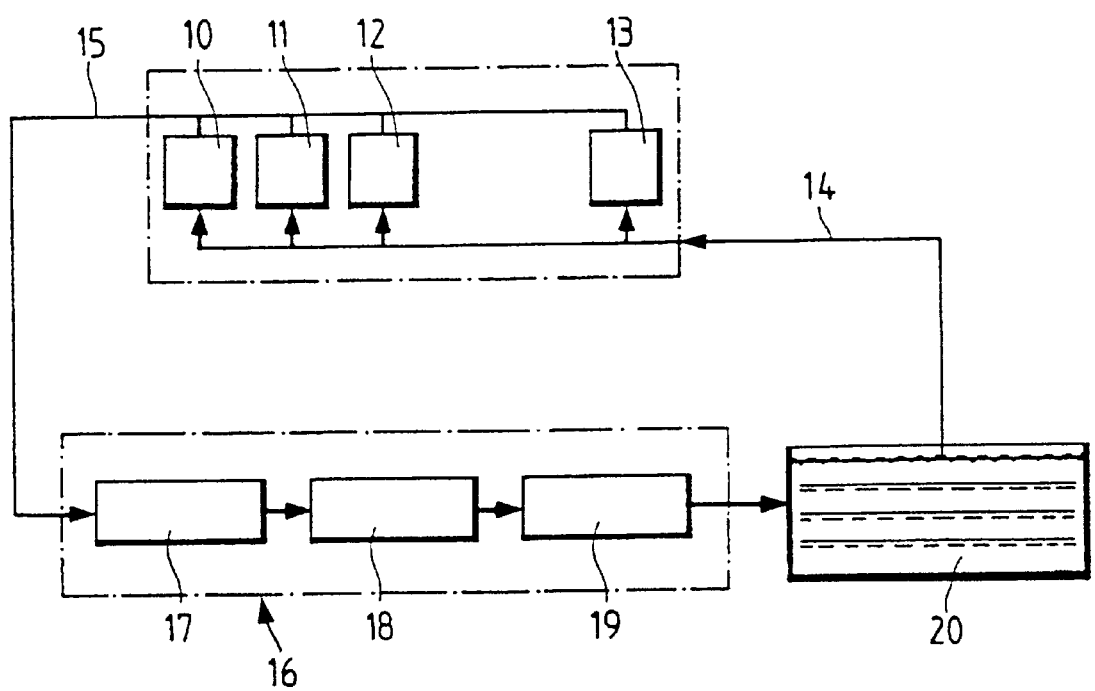
FIG. 1 shows a processing system for a processing liquid.

The processing system according to FIG. 1 schematically shows several machine tools 10, 11, 12, 13. Processing liquid, particularly a cooling lubricant emulsion, is fed to these machine tools by way of the pipe 14. By way of the pipe 15, the cooling lubricant emulsion loaded with suspended solids or dirt particles and other impurities reaches an emulsion processing system 16. In the emulsion processing system, the separating of particles or suspended solids takes place in a filtering system 17. In another device 18, the separating of foreign oil takes place, and in another filtering system 19, the removal of superfine particles takes place from the emulsion by way of, for example, an emulsion separator. The purified and processed emulsion arrives in a collecting tank 20 and is available again to the processing operation. The transporting of the cooling lubricant emulsion takes place by way of delivery pumps which are not shown here.

Figure 2:
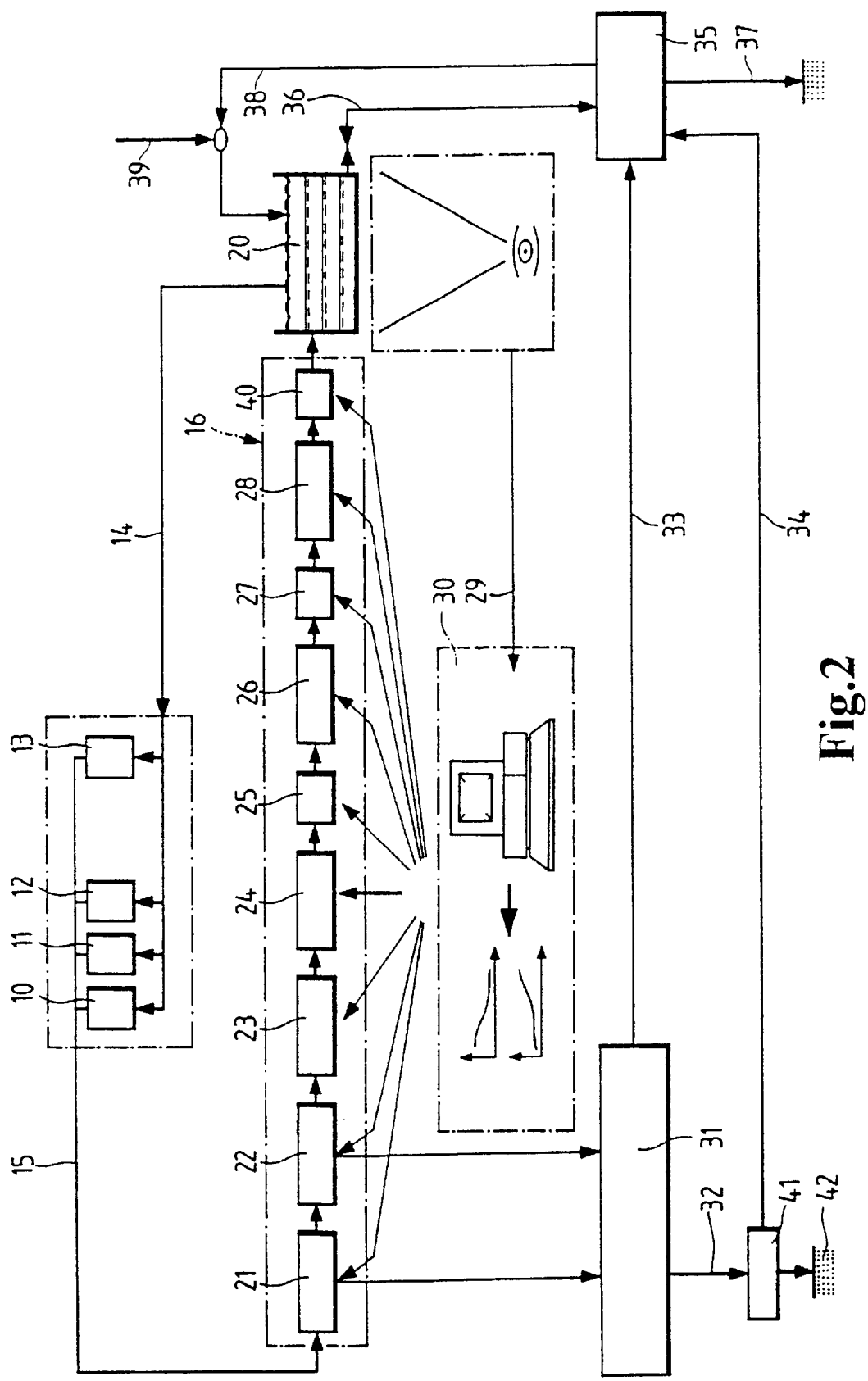
FIG. 2 shows an integrated system concept for monitoring and processing the processing liquid as well as subsequent disposal process steps (including wire drawing, cold rolling facilities)
Figure 3:
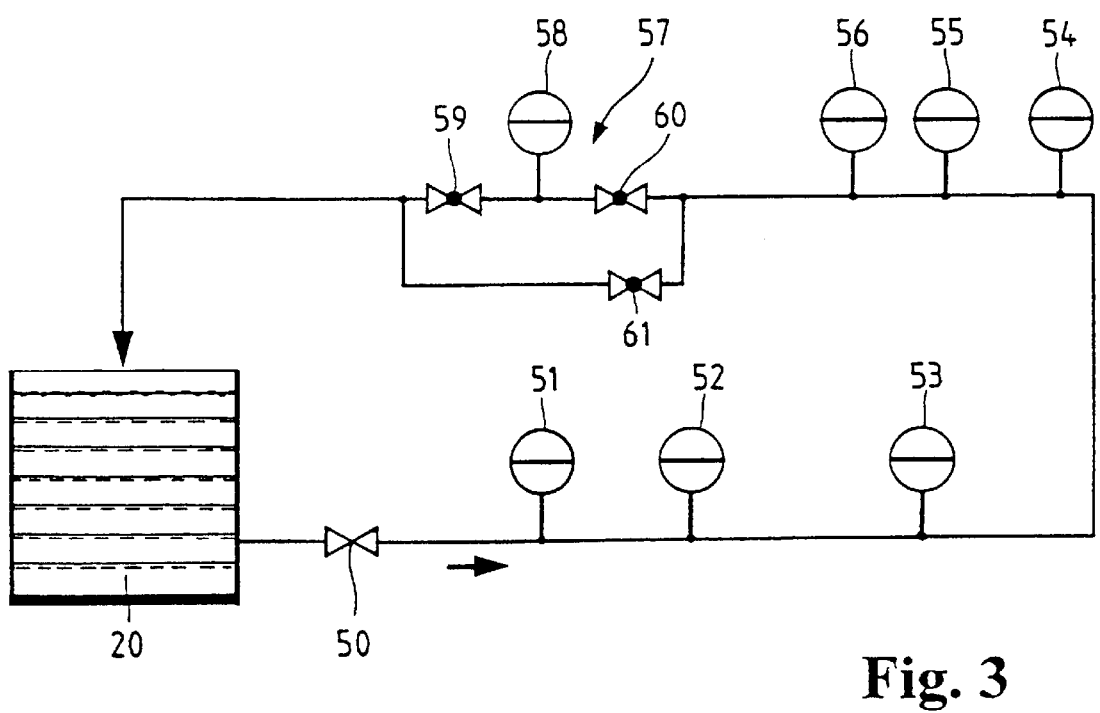
FIG. 3 shows a schematic illustration of the sensors for detecting data of a processing liquid.

FIG. 2 shows a device for monitoring the processing liquid. Here also, the machine tools 10, 11, 12, 13 are to be supplied with processed emulsion by way of the pipe 14. The loaded emulsion is supplied by way of the pipe 15 to the emulsion processing and care system 16. The processed emulsion is available in a tank 20. In this tank 20, measuring quantities are now determined by means of suitable sensors. This involves one or the following of the measuring quantities mentioned in the following: The temperature, the pH-value, the concentration, the conducting capacity, the corrosiveness, the protection against corrosion, foreign oil, suspended solids, foreign substances, microorganisms, germs, yeast fungi, bacteria, abrasiveness, nitrate, nitrite, water hardness, interfering ions, dispersed air, foamed chloride. Naturally, other measuring quantities can be detected by means of suitable sensors.

These measurement parameters are transmitted via a data transmission or a remote data transmission 29 to a diagnostic system 30. This diagnostic system has the function of analyzing the condition of the KSS medium in that it compares the actual values with prescribed target values, recognizes trends with respect to the course of the actual values, and works out possible control strategies. Naturally, an analysis of the measured parameters is also conceivable at the site.

Based on the defined concept with respect to the automatic control or control of the quantities within the cooling lubricant emulsion detected by measuring, interventions into the emulsion take place directly or by way of remote data transmission for the processing and care of the emulsion. The interventions may also take place manually; that is, by a visual monitoring of the data, certain constituents of the emulsion are changed. Thus, the emulsion is purified corresponding to its degree of contamination, for example, by way of a filtering system 21. Foreign oil is removed from the emulsion by way of a corresponding system 22. Another filtering element 23 is capable of removing superfine particles from the emulsion. A system 24 for reducing the microorganisms is also controlled by means of the diagnostic system 30. The pH-value is set and regulated by way a system 25. The corrosiveness can be changed by way of a system 26. The temperature is controlled by way of a suitable device 27. The concentration of the emulsion, that is, the ratio between water and oil is controlled by way of a system 28. Additional process steps can also be carried out. FIG. 2 illustrates this possibility by means of the block box 40.

The change of the emulsion with respect to its composition and operability increases the process safety and therefore the useful life. As a result, the processing of the coolant lubricant emulsion is independent of the type of the processing method at the machine tools. It is unimportant whether the machine tools are carrying out a uniform or a different processing method. The emulsion is only monitored and optimized corresponding to its characteristics. This also applies to processing methods such as wire drawing, cold rolling and forming manufacturing methods.

The diagnosis of the measured parameters can take place automatically. Naturally, it is also possible to carry out manual interventions in the system and thus implement a semi-automatic control or a control of the parameters.

The entire device for monitoring the processing liquid can have a device 31 for the dewatering of filter cakes or the removal of oil from grinds, as a special feature. The fraction of solids from this device is supplied by way of a pipe 32 or a delivery device to a chip washing system. The de-oiled chips arrive in a corresponding receiving device or in a recycling system.

The liquid fraction from the filter cake dewatering and from the chip washing system arrives by way of pipes 33, 34 at a device for separating emulsions. The old emulsion from the tank 20 can be supplied to this device via pipe 36. The emulsion separation effects a separation of oil and water. The oil arrives by way of a pipe 37 at a processing system which is not shown here. The water can be returned into the tank 20 by way of pipe 38. Fresh water or emulsion concentrate can additionally be fed to the tank by way of a pipe 39. Sensors arranged in the tank 20 are provided with one or several suitable devices which maintain the operability of the sensors. This may be a washing device, a corresponding cleaning device or a similar device. The sensors are calibrated at regular intervals; that is, the diagnostic system 30 checks and corrects the sensor-specific signals.

A partial flow from the tank 20 with the processing liquid arrives by way of a valve 50 at the temperature sensor. Subsequently, a density measurement takes place by means of the sensor 52, and the conducting capacity is measured by means of the sensor 53. A sensor 54 is provided for determining cloudiness. The sensor 55 is a redox measuring transducer for determining the corrosion behavior. After the pH-value sensor 56, the liquid is transported into a closed system 57 This closed system is used for measuring the consumption of oxygen for a certain time period. An oxygen sensor 58 is provided for this purpose. Following the measuring cycle, the processing liquid is returned to the tank 20.

So that, during the determination of the oxygen content of the sample, the additional series of measurements will not be interrupted, three valves 59, 60, 61 are situated in the loop. During the measuring of the oxygen content, valves 59, 60 are closed and valve 61 is open. For receiving a new sample for measuring the oxygen, valve 61 will be closed and valves 59, 60 will be opened.

What is claimed is:

1. An apparatus for monitoring a processing liquid, said apparatus comprising:

at least one processing tank;

a closed chamber;

at least one sensor for measuring a parameter of said processing liquid and generating a monitoring signal indicative of the condition of said liquid; a device for maintaining the operability of said at least one sensor; a signal processor for receiving said monitoring signal from said sensor, evaluating the condition of said processing liquid based on said monitoring signal and generating a control signal based on the condition of said processing liquid; and a device responsive to said control signal for adjusting the composition of said processing liquid on the basis of specified criteria or nominal quantities;

wherein said sensor is an oxygen sensor mounted in said closed chamber into which said processing liquid can be introduced, and said sensor measures oxygen consumption in said processing liquid as a function of temperature, and said signal processor determines an aerobic microorganism content of said processing liquid based on the measured oxygen consumption and the temperature; and wherein said closed chamber is separate from said at least one processing tank.

2. An apparatus according to claim 1, wherein said monitoring signal is supplied to said signal processor by remote data transmission.

3. An apparatus according to claim 1, further comprising a filtering system for mechanical purification of said processing liquid.

4. An apparatus according to claim 1, further comprising separating means for separating said processing liquid into individual constituents.

5. An apparatus according to claim 4, wherein said separating means comprise an emulsion separator.

6. A method for monitoring a processing liquid, said method comprising the steps of:

introducing a processing liquid into a closed chamber;

contacting the processing liquid in said closed chamber with a sensor which senses an oxygen content of the liquid and monitoring the liquid for changes in oxygen content, and deriving a value for microorganism content of said liquid from changer in the oxygen content of the liquid;

wherein said processing liquid is stored in at least one processing tank and said at least one processing tank is separate from said closed system, and wherein said sensor is provided ,vith means for maintaining the operability of the sensor.

7. A method for maintaining a processing liquid, said method comprising the steps of:

contacting said processing liquid with at least one oxygen sensor mounted in a closed chamber which generates a monitoring signal indicative of the oxygen consumption of said processing liquid as a function of temnperature;

transmitting said monitoring signal to a signal processor, evaluating the microorganisn content of said processing liquid based on the oxygen consumption and the temperature and generating a control signal based on the condition of said processing liquid, and transmitting said control signal to can apparatus for adjusting the condition of said processing liquid, so as to maintain the condition of said liquid at a desired target value;

wherein said processing liquid is stored in at least one processing tank and said at least one processing tank is separate from said closed system, and wherein said at least one sensor is provided with means for maintaninlg the operability of the sensor.

* * * * *